United States Patent
Schermer et al.

(10) Patent No.: US 6,631,211 B1
(45) Date of Patent: Oct. 7, 2003

(54) INTERACTIVE SYSTEM FOR ANALYZING SCATTER PLOTS

(75) Inventors: Mack J. Schermer, Belmont, MA (US); Todd J. Stephan, Santa Clarita, CA (US)

(73) Assignee: PerkinElmer LAS, Inc., Boston, MA (US)

( * ) Notice: Subject to any disclaimer, the term of this patent is extended or adjusted under 35 U.S.C. 154(b) by 0 days.

(21) Appl. No.: 09/349,334

(22) Filed: Jul. 8, 1999

(51) Int. Cl.[7] ................................................ G06K 9/62
(52) U.S. Cl. ........................ 382/225; 209/582; 378/6; 378/70
(58) Field of Search ........................ 382/225; 704/245; 209/576, 577, 578, 579, 580, 581, 582; 378/5, 6, 7, 49, 70

(56) References Cited

U.S. PATENT DOCUMENTS

| | | | |
|---|---|---|---|
| 3,638,188 A | * 1/1972 | Pincoffs et al. | 382/201 |
| 4,732,157 A | 3/1988 | Kaplan et al. | |
| 4,845,653 A | 7/1989 | Conrad et al. | |
| 4,987,086 A | 1/1991 | Brosnan et al. | |
| 5,075,896 A | * 12/1991 | Wilcox et al. | 382/225 |
| 5,365,455 A | * 11/1994 | Tibbetts et al. | 702/20 |
| 5,375,175 A | * 12/1994 | Kino et al. | 356/636 |
| 5,433,199 A | 7/1995 | Cline et al. | |
| 5,458,126 A | * 10/1995 | Cline et al. | 324/309 |
| 5,519,789 A | * 5/1996 | Etoh | 382/225 |
| 5,544,267 A | * 8/1996 | Mahoney et al. | 358/400 |
| 5,703,959 A | * 12/1997 | Asano et al. | 382/133 |
| 5,732,043 A | 3/1998 | Nguyen et al. | |
| 5,861,891 A | * 1/1999 | Becker | 345/619 |
| 5,999,639 A | * 12/1999 | Rogers et al. | 382/132 |
| 6,118,891 A | * 9/2000 | Funada | 382/125 |
| 6,141,443 A | * 10/2000 | Nakao et al. | 382/174 |
| 6,272,250 B1 | * 8/2001 | Sun et al. | 382/155 |
| 6,307,965 B1 | * 10/2001 | Aggarwal et al. | 382/225 |
| 6,345,119 B1 | * 2/2002 | Hotta et al. | 382/186 |
| 6,453,246 B1 | * 9/2002 | Agrafiotis et al. | 702/27 |

FOREIGN PATENT DOCUMENTS

| | | |
|---|---|---|
| EP | 0 350 837 | 1/1990 |
| EP | 0 780 680 | 6/1997 |

OTHER PUBLICATIONS

Excerpt from conference proceedings book for Bioinformatics and Genome Research Conference held Jun. 14–15, 1999.

Paul T. Spellman et al., "Comprehensive Identification of Cell Cycle–regulated Genes of the Yeast Saccharomyces Cerevisiae by Microarray Hybridization", Dec. 1998, pp. 3273–3297.

Matthew J. Marton et al., "Drug Target Validation and Identiifcation of Secondary Drug Target Effects Using DNA Microarrays", Stanford University, pp. 1293–1301.

* cited by examiner

*Primary Examiner*—Amelia M. Au
*Assistant Examiner*—Anand Bhatnagar
(74) *Attorney, Agent, or Firm*—Cesari and McKenna, LLP

(57) ABSTRACT

A scanner system analyses data plotted in a scatter plot in accordance with user-specified criteria or statistical measures from the data population, to produce a scatter plot that displays in the plotted data the boundaries for the selection of out-lyer points and/or otherwise visually denotes in the plotted data which points are the out-lyer points. The scanner system analyzes the underlying data based on user-specified differential expression ratios, or based on criteria associated with the statistics of the data population, to produce out-lyer boundaries that are represented by diverging lines. Alternatively, the system may analyze the underlying data based on absolute expression levels, to produce boundaries that are represented in the plot by lines that meet at an identity line of slope 1. The scanner system may also combine several criteria and produce boundaries that denote as out-lyers the data that, for example, show both sufficient differential expression and also include individual expressions that are sufficiently above an associated noise floor.

50 Claims, 6 Drawing Sheets

INTERACTIVE SYSTEM FOR ANALYZING SCATTER PLOTS

BACKGROUND OF THE INVENTION

Microarray biochips are being increasingly used for the performance of large numbers of closely related chemical tests. For example, to ascertain the genetic differences between lung tumors and normal lung tissue one might deposit small samples of different DNA sequences on a microscope slide and chemically bond them to the glass. Ten thousand or more such samples can easily be arrayed as dots on a single microscope slide using mechanical microarraying techniques. Next, sample RNA is extracted from normal lung tissue (a control sample) and from a lung tumor (a test sample). The RNA represents all of the genes expressed in these tissues and the differences in the expression of RNA between the diseased tissue and the normal tissue can provide insights into the cause of the cancer and perhaps point to possible therapeutic agents as well. The "probe" samples from the two tissues are labeled with different fluorescent dyes. A predetermined amount of each of the two samples is then deposited on each of the microarray dots where they competitively react with the DNA molecules. The RNA molecules that correspond to the DNA strands in the microarray dots bind to the strands and those that do not are washed away.

The slide is subsequently processed in a scanner that illuminates each of the microarray dots with laser beams whose wavelengths correspond to the fluorescences of the labeling dyes. The fluorescent emissions are sensed and their intensity measured to ascertain, for each of the microarray dots, the degree to which the RNA samples correspond to the respective DNA sequences. In the experiment outlined above the image scanner separately senses the two fluorescences, and thereby provides for each dot two numerical values, or "expression levels," that represent reactions of the RNA extracted from the normal and diseased tissues. The scanner may then plot the data on a scatter plot, which has axes that correspond, respectively, to the intensity levels of the two fluorescences. A user then analyses the pattern of the data on the scatter plot.

The purpose of these experiments is to identify individual data points that are located sufficiently far from an identity line, i.e., a line in which the two intensities are the same, or some other closed-form mathematical function to denote a significant response difference. These points are commonly referred to as "out-lyers." In other types of experiments, the purpose is to determine whether the data produces a scatter plot pattern that approximates the identity line, some other straight line, or some other function, such as, for example, a parabola. In these experiments, the observer of the plot judges the closeness of the correlation between the plotted data points and the locus of the line produced by the mathematical function. The invention described below is concerned with the types of experiments in which out-lyers are identified.

The out-lyers that are of particular interest in the experiment described above correspond to genes that are sufficiently "differentially expressed." Differential gene expression is most often measured as the ratio of the control tissue expression level and the test tissue expression level, where an expression level is the absolute value of the associated fluorescence intensity.

Genes that are nearly equally expressed in both the control tissue and the test tissue will produce scatter plot data that are on or near the identity line, while genes that are differentially expressed will produce plot data that are farther from the identity line. Genes with low expression levels will produce plot data that are near the origin, or (0,0) point, regardless of their differential expression levels. The low expression levels expression can indicate lower data reliability, due to a low signal-to-noise value of that experiment. Accordingly, the experimenter may choose to omit the data from these genes from further study.

The identification of the genes that are candidates for further study is often done subjectively by visually judging which plotted points of the scatter plot are sufficiently far from the origin, that is, have high enough signal levels to justify confidence in the data, and/or are sufficiently far from the identity line, and thus, strongly differentially expressed. Known computer programs designed for the analysis of differential gene expression data often display a scatter plot, and provide to the user a mechanism to identify individual points of interest. For each identified point, the program may, for example, display or otherwise process the underlying gene data that generated the plotted point. Once the plotted points that meet the selection criteria have been identified by the user, the user may then collect or otherwise process the results for further analysis and experimentation.

It is simple to make qualitative judgements of the characteristics of individual plotted points in scatter plots that are comprised of a relatively small number of points. However, it is difficult to judge the differential expression ratio of the points, and/or to judge which points are just above or just below any particular expression level threshold. Further, these judgments and the identification of points of interest are more difficult to make with scatter plots that contain hundreds or thousands of data points. Accordingly, they are difficult for use with scatter plots associated with microarrays.

SUMMARY OF THE INVENTION

The inventive scanner system analyses data plotted in a scatter plot in accordance with user-specified criteria or statistical measures from the data population, to produce a scatter plot that displays in the plotted data the boundaries for the selection of out-lyer points and/or otherwise visually denotes in the plotted data which points are the out-lyer points. The scanner system may, for example, analyze the underlying data based on user-specified differential expression ratios, or based on criteria associated with the statistics of the data population, to produce out-lyer boundaries that are represented by diverging lines. Alternatively, the system may analyze the underlying data based on absolute expression levels, to produce boundaries that are represented in the plot by lines that meet at the identity line. The scanner system may also combine several criteria and produce boundaries that denote as out-lyers the data that, for example, show both sufficient differential expression and also include individual expressions that are sufficiently above an associated noise floor.

The scanner system also allows a user to inter-actively specify various selection criteria, for example, various differential expression ratios, and view the associated boundaries. The user can then determine which ratio is appropriate for the particular data. Alternatively, the user may specify desired numbers of out-lyer points, and have the system set the appropriate differential expression ratios for the data population. The system then produces plots that display the associated boundaries.

The system then "filters" the data based on the user and/or system specified selection criteria, and retains in a file for further study the underlying gene-specific information associated with the data points that are located outside of the boundaries.

BRIEF DESCRIPTION OF THE DRAWINGS

The invention description below refers to the accompanying drawings, of which.

DETAILED DESCRIPTION OF AN ILLUSTRATIVE EMBODIMENT

Figure 1:
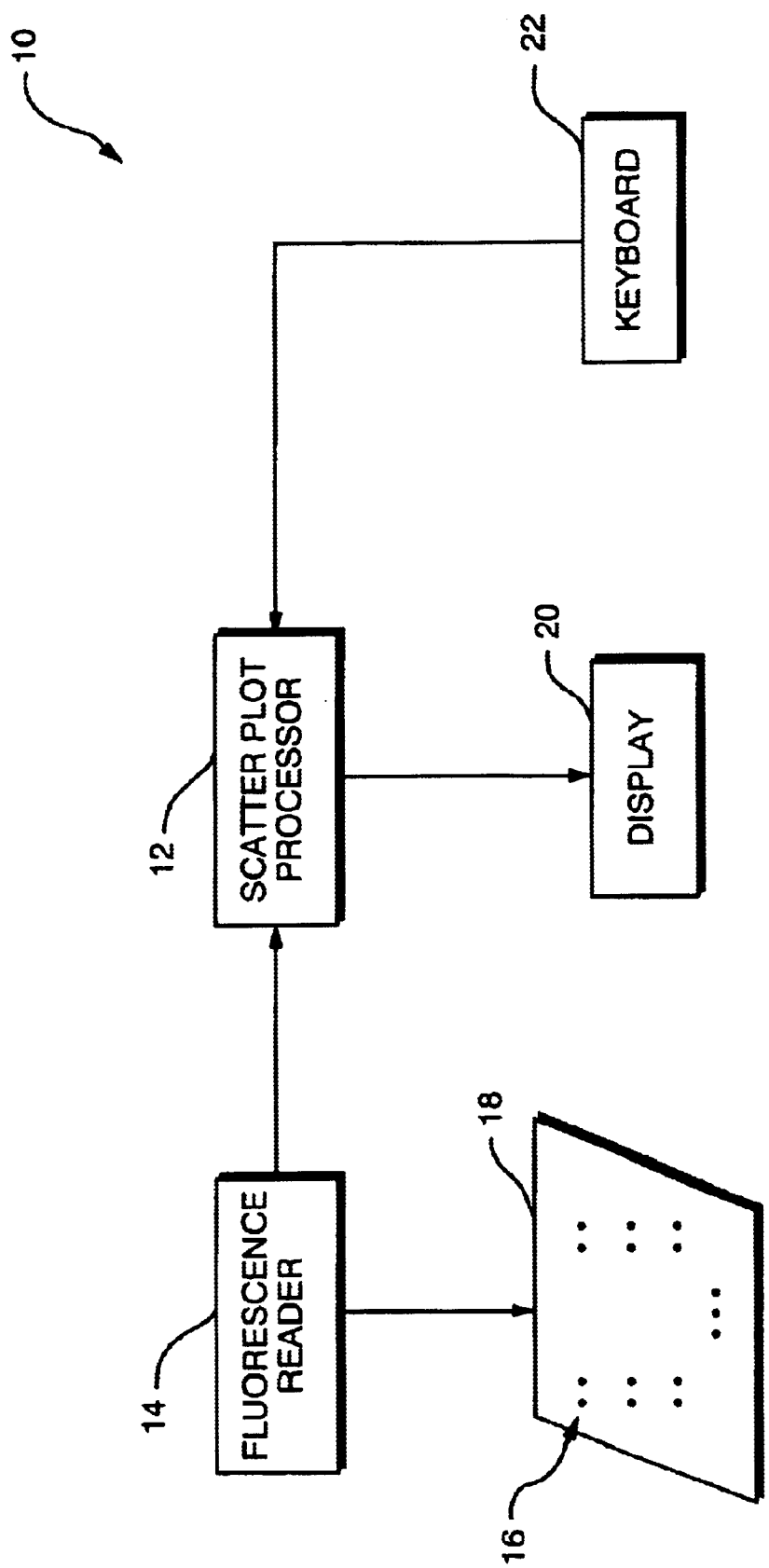
FIG. 1 is a functional block diagram of a system constructed in accordance with the invention.

Referring now to FIG. 1, a system 10 for analyzing scatter plot information includes a scatter plot processor 12 that receives information relating to fluorescent Is intensities from a fluorescence reader 14. The fluorescence reader 14 operates in a conventional manner to determine the different fluorescent intensities of dots 16 on a microarray 18. The microarray 18 generally includes thousands of target genes in the form of microarray dots 16 that, based on the genes present in control and test probe samples, respond appropriately to the fluorescent wavelengths associated, respectively, with the control and test tissue fluorescent dyes. For each dot, the fluorescence reader 14 provides to the scatter plot processor 12 both a control expression level and a test expression level.

The scatter plot processor 12 produces a scatter plot that includes a data point for each dot on the microarray, and a display unit 20, such as a computer monitor, displays the plot. As discussed in more detail below, the scatter plot processor also adds boundary lines to the scatter plot, to denote that certain data points are out-lyers, and thus, candidates for further study. A user may interactively set the boundary conditions by specifying selection criteria through a keyboard 22 or other data input device. Also, the user may inter-actively change the selection criteria, and the system then draws new boundaries. The user can thus modify the selection criteria to fit the data population.

Figure 2:
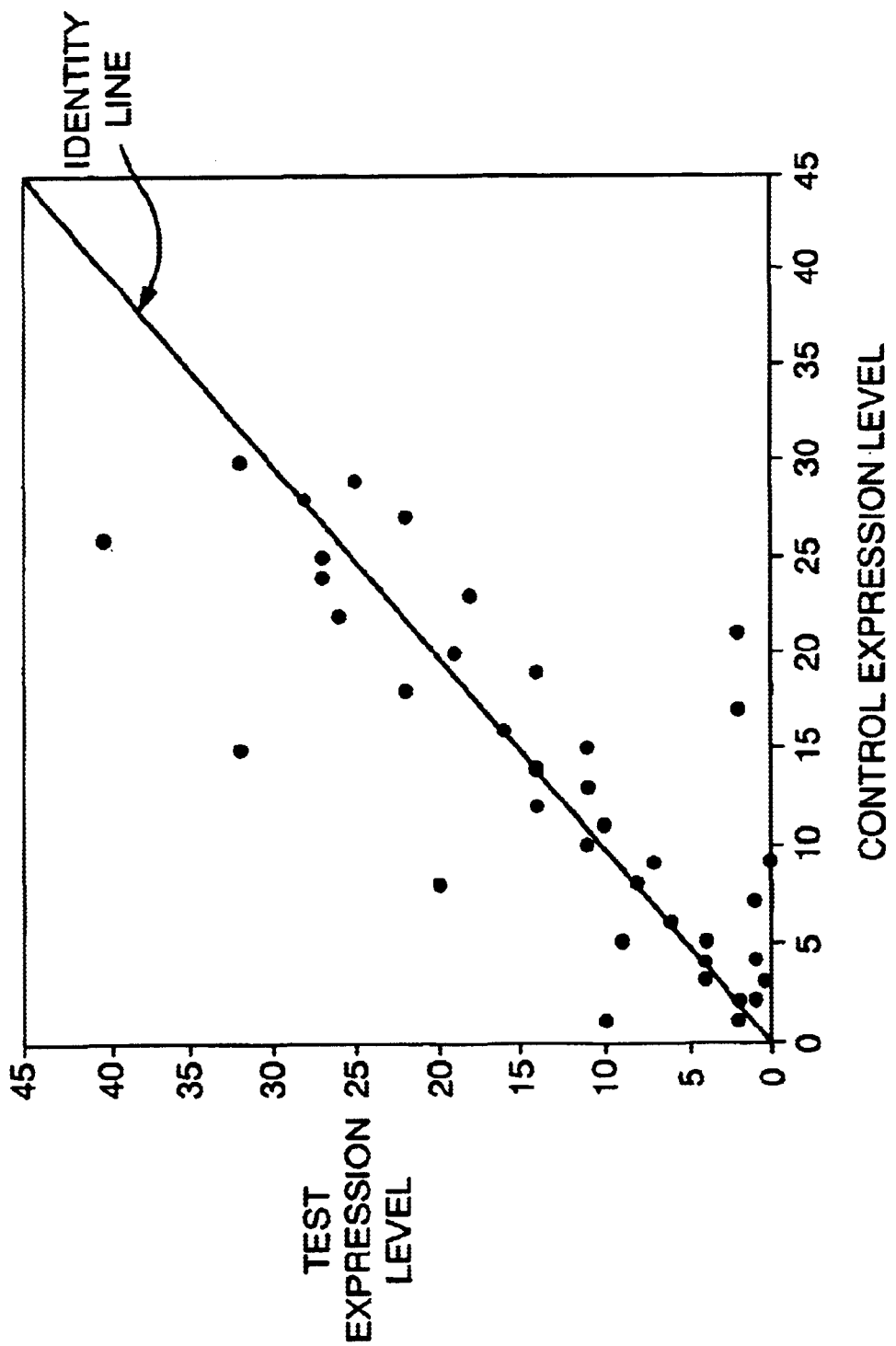
FIG. 2 is a drawing of a scatter plot produced by the system.

For ease of understanding, we include drawings that depict relatively small numbers of data points. In use, the system produces scatter plots with hundreds or thousands of data points. Referring now to FIG. 2 a scatter plot is shown before the boundary lines are supplied. The scatter plot includes an identity line that denotes equal expressions for both types of fluorescence. The data points on the identity line thus represent genes that are similarly expressed in the control tissue and the test tissue, and are of little interest for further study. Conversely, the points that are some distance away from the identity line represent genes that differ between the control sample and the test sample. The genes that are sufficiently differentially expressed are of interest for further study to determine, for example, how the healthy tissue differs from the diseased tissue.

Figure 3:
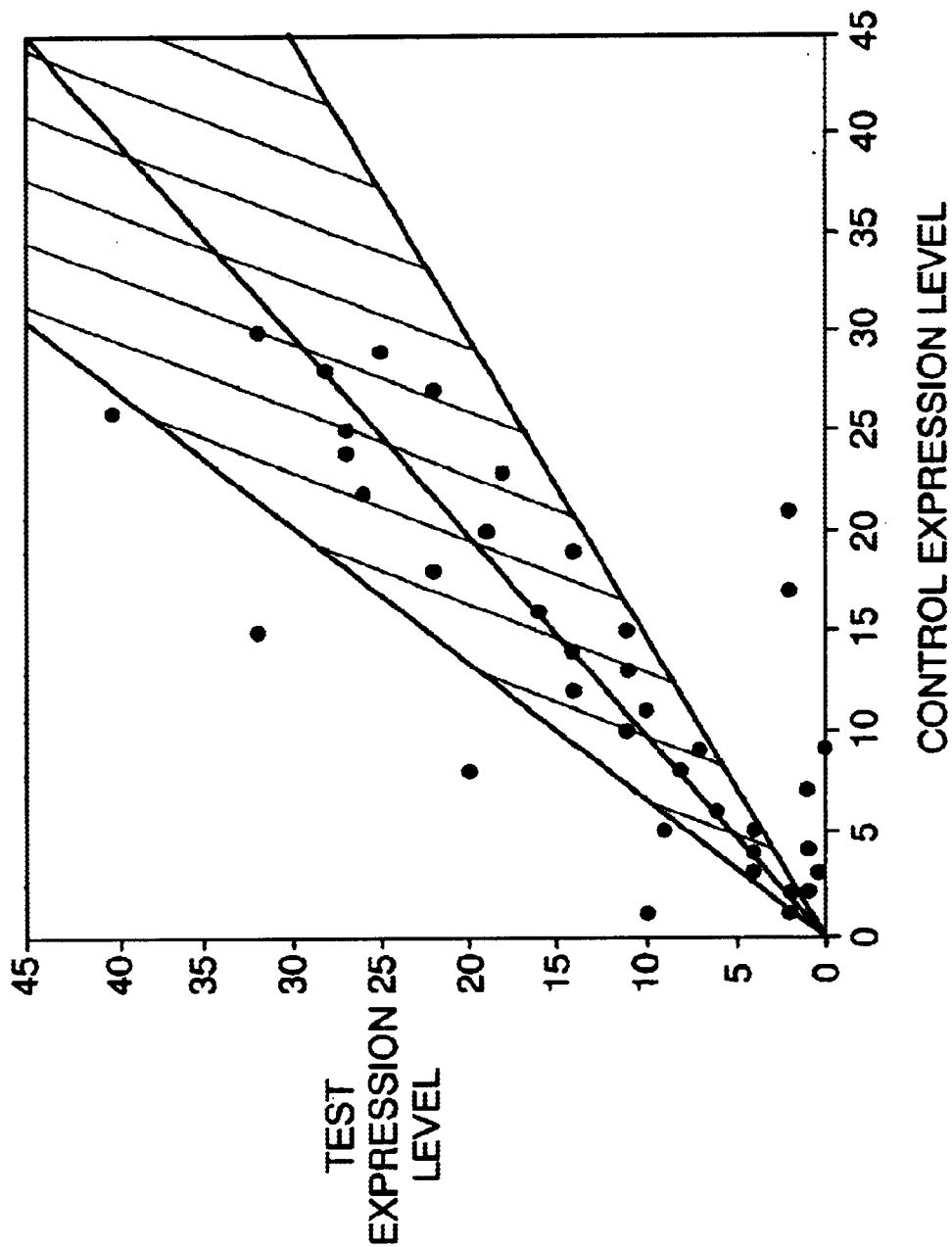
FIGS. 3–6 are drawings of scatter plots containing boundary lines.

A user may specify the selection criteria that distinguish out-lyer points from other points as, for example, a particular ratio of test expression level to control expression level, that is, as a differential expression ratio. As shown in FIG. 3, the associated boundary lines 20 and 22 start close to the origin and diverge, with each boundary line having a slope that is associated with the specified differential expression ratio. The drawing depicts boundaries associated with a differential expression ratio of 1.5. The boundary line 20 has a slope of 1.5 and the boundary line 22 has a slope of $$\frac{1}{1.5}$$

or 0.66. The data points that lie between the two boundary lines are deemed to be sufficiently close to the identity line, based on the user-specified criteria, to be of little interest for further study. The points that lie outside of the boundary lines meet the user-specified criteria for out-lyers. As shown in the drawing, the system may include cross-hatching to further distinguish the non-selected points in the plot. Alternatively, the system may dim the points inside the boundaries, change their color or similarly change their visual properties with respect to the point outside the boundaries.

To determine if the boundary criteria are appropriate, a user may look at one or more of the data points in more detail. The user thus selects the point or points of interest, and the scatter plot processor 12 displays some or all of the underlying gene information for the points. The user may then determine that the boundary lines should be re-drawn to include or exclude certain points for further study. The user next specifies a different ratio, as appropriate.

Further, as discussed above, the scatter plot processor 12 filters the data based on the boundaries, and stores in a data file the underlying gene-specific information for each of the out-lyer points. The user may then study or analyze this information.

After viewing the results, a user may wish to specify selection criteria based on the data population. For example, the user may specify that the out-lyer points must be more than one standard deviation from the identity line. The scatter plot processor will then analyze the data population and depict the applicable boundaries in the scatter plot display. A user may next, as discussed above, select individual data points and review the underlying data to determine if the selection criteria is appropriate. At the same time, the scatter plot processor filters the data and preserves in a data file the underlying gene information relating to the out-lyer points as defined by the new boundaries.

Figure 4:
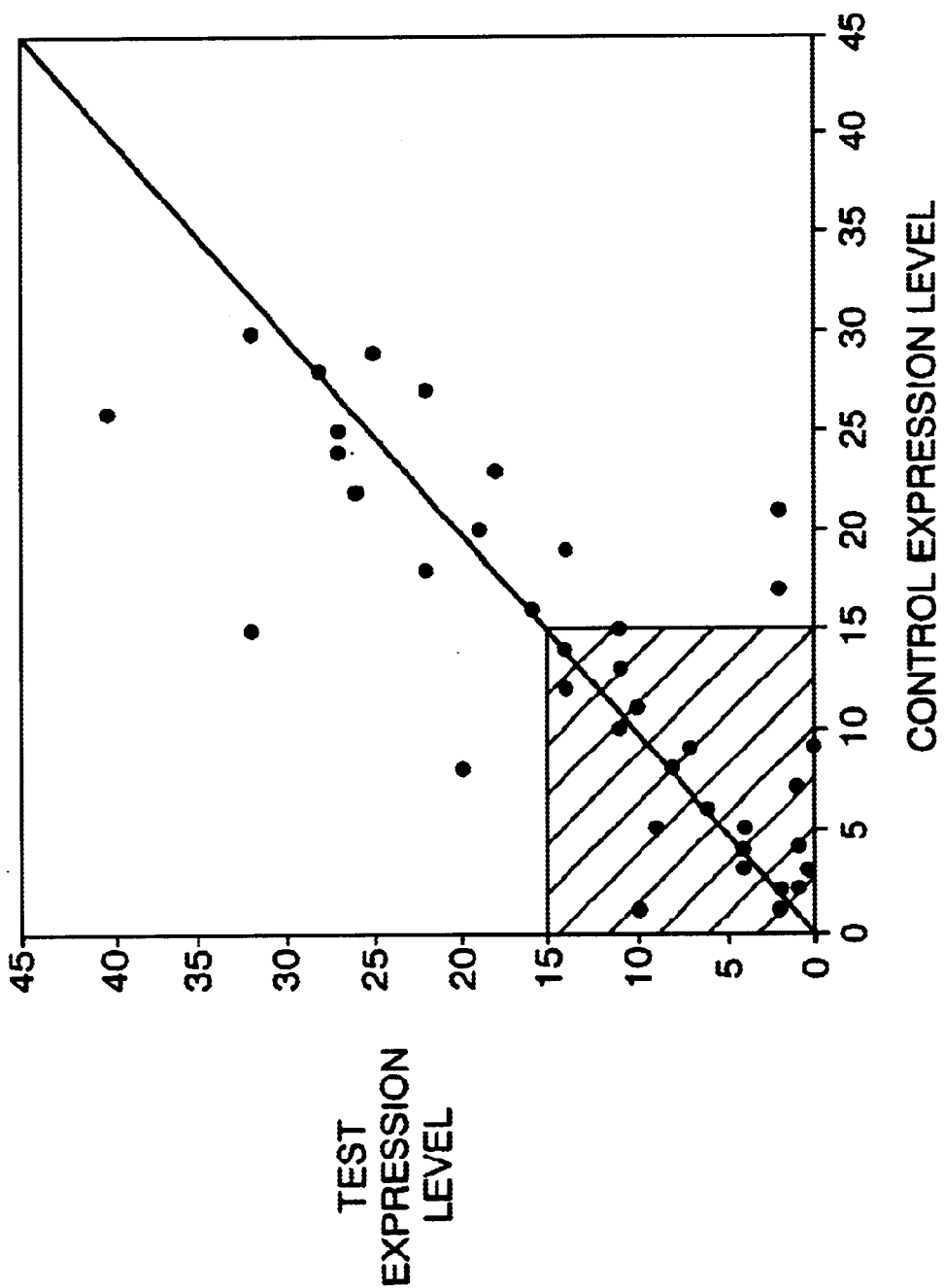

Referring now to FIG. 4, the user may base the selection criteria on the individual expression levels. The points nearest the origin, whether they are inside or outside of the differential expression boundaries, represent data in which the fluorescence intensities indicate relatively low response to the test or control samples. Indeed, some of these points may be within the noise level of the system. Accordingly, a user may specify a particular noise floor, and the scatter plot processor will then define and depict noise boundaries that set a minimum expression level for the out-lyer points. As depicted in FIG. 4, the noise boundaries 40 and 42 represent expression levels of 15. The out-lyer points thus have at least one of the control and test expression levels above 15. The selection criteria for the noise floor may instead be a particular percentage of the data points, and the system then sets the noise boundaries based on the data population.

Figure 5:
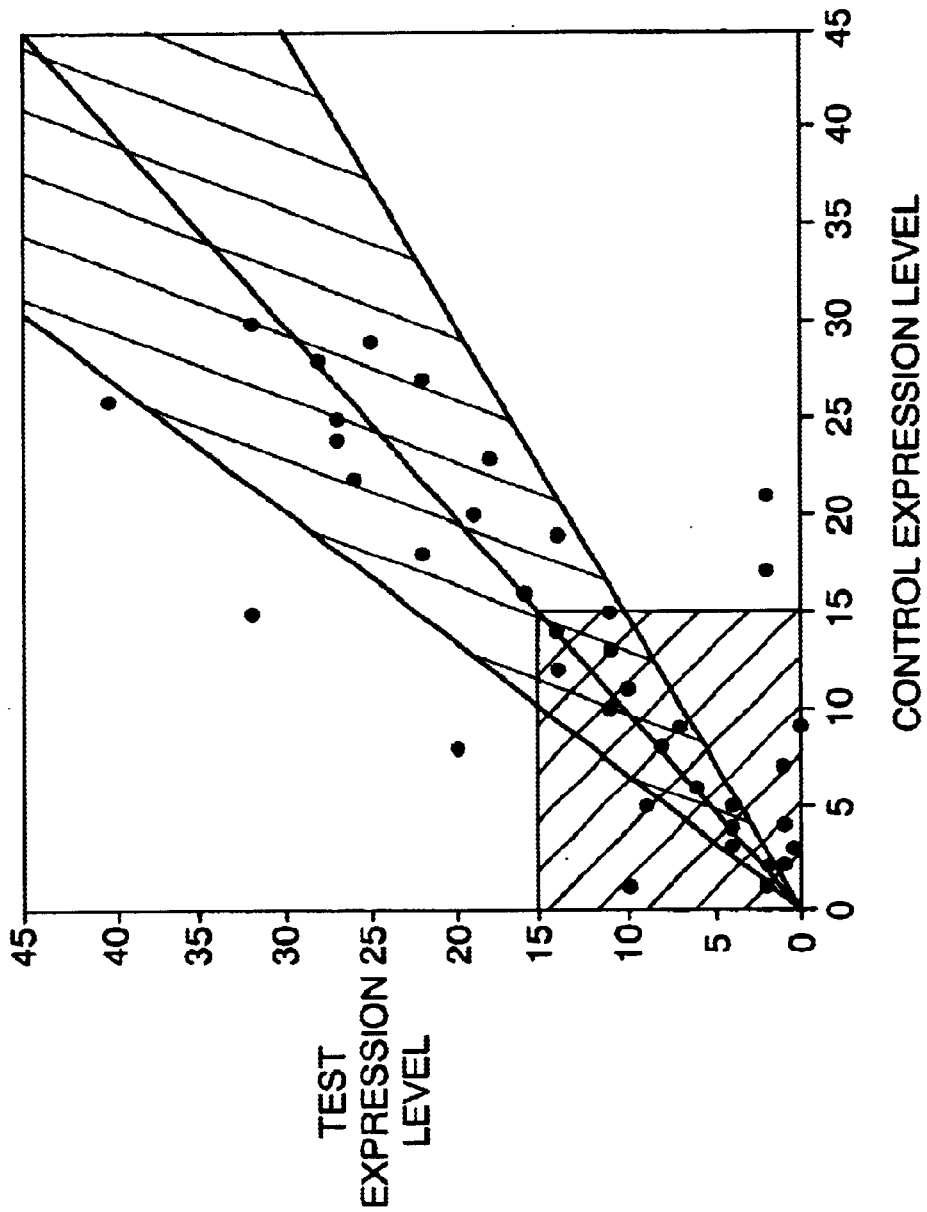

As shown in FIG. 5, the system may depict both noise boundaries and differential expression ratio boundaries on the same scatter plot. The out-lyer points are then the points that are outside both sets of boundaries.

The selection criteria for the noise floor may instead be a particular percentage of the data points. The system then sets the noise boundaries based on the data population.

Figure 6:
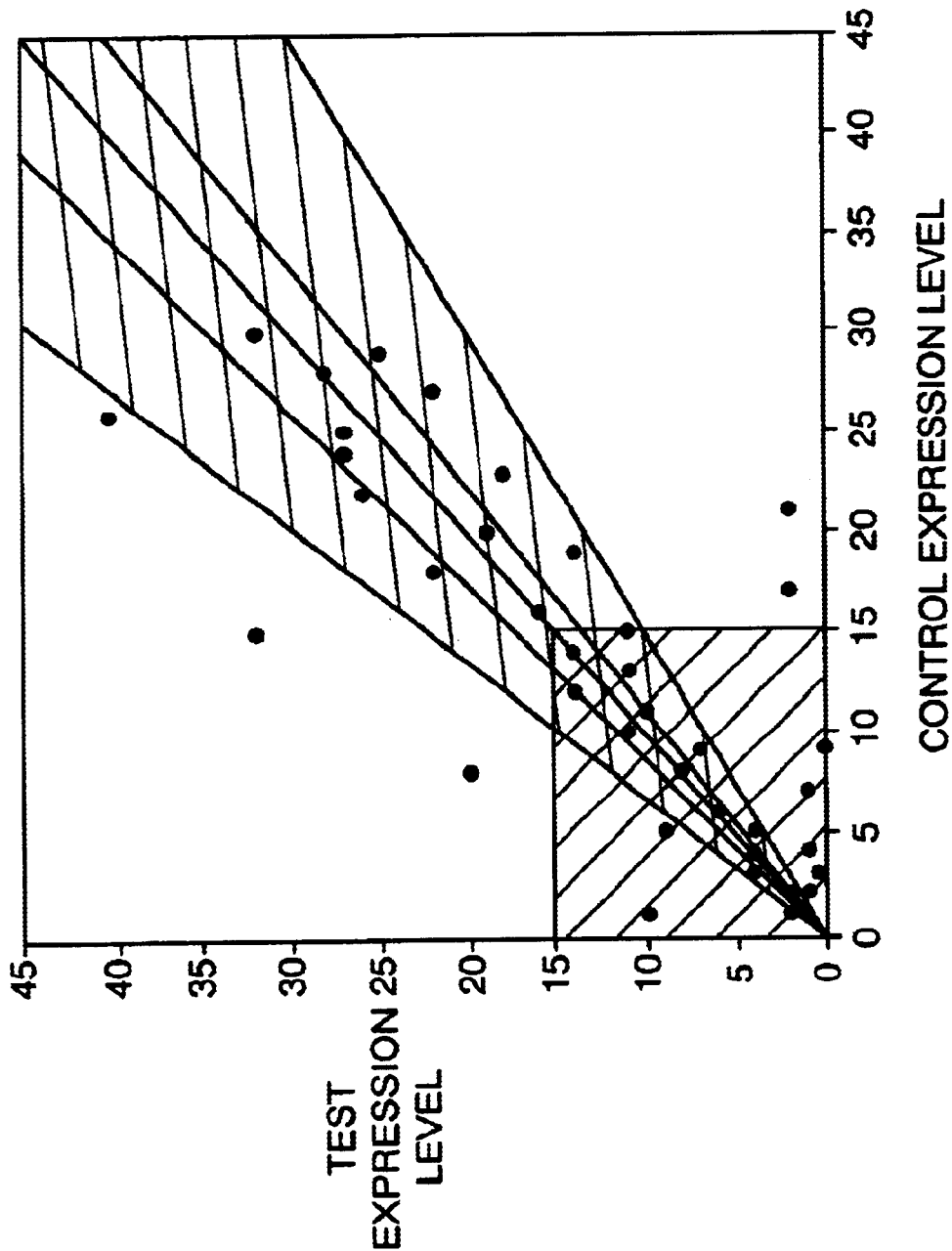

As shown in FIG. 6, a user may specify a plurality of boundary conditions, such that the scatter plot includes multiple sets of boundary lines that represent, for example, several differential expression levels. The scatter plot processor can then filter the data with respect to each of the various boundary conditions, and set up a plurality of data files that contain information relating to out-lyers as defined by the boundaries of interest. Alternatively, the scatter plot processor can filter the data based on particular, selected boundary lines.

The user may instead specify the selection criteria as a particular number of out-lyer points. For example, the user may specify that it wishes to see the boundary conditions that define five points as out-lyers. The scatter plot processor then determines an applicable differential expression ratio that satisfies the user's criteria, and displays the scatter plot with lines denoting the applicable boundaries. The system may also include the applicable differential expression ratio in the display. Again, the user may specify different selection criteria, to re-position the boundary lines or to superimpose additional boundary lines on the display. The scatter plot processor may then save information relating to the various boundary conditions and the underlying data for each of the out-lyer points in associated data files.

We have discussed the scatter plot system in terms of analyzing differential gene expression. However, the system may be used to analyze any type of scatter plot and designate the out-lyer points in the scatter plot. We have discussed including boundary lines in the scatter plot as a way of visually distinguishing out-lyer points from the other data points. The out-lyer plot points may instead be distinguished by plotting them in colors that differ from the colors of the non-selected plot points, by depicting the background beyond the boundaries in different colors, and so forth. Further, the system may produce the scatter plot with X and Y axes that have logarithmic scales or axes with different scales from one another. The scales may be specified by the user, or the system may set them based on the data population.

What is claimed is:

1. A system for analyzing differential gene expression data, the system including:
   A. means for producing and displaying a scatter plot that contains a plotted point for each of the differential gene expression data,
   B. boundary means for
      i. determining boundaries for segmenting the data based on specified selection criteria and displaying the boundaries in the scatter plot,
      ii. determining different boundaries for segmenting the data in response to a user interactively specifying changes to the election criteria by setting new differential expression ratios to contrast experimental expression levels to control expression levels in the data and displaying the different boundaries in the scatter plot, and
   C. a filtering means for collecting the data corresponding to the plotted points that are
      i. outside of the respective boundaries, or
      ii. inside the respective boundaries.

2. The system of claim 1 wherein the filtering means further records the collected data in a computer file.

3. The system of claim 1, wherein the boundary means determines the boundaries based on a specified differential expression ratio, with one expression corresponding to a variable associated with an x-axis and the other expression corresponding to a variable associated with a y-axis.

4. The system of claim 3 wherein the boundary means produces boundary lines that diverge from an x=0, y=0 point and have slopes that are associated with the specified differential expression ratio.

5. The system of claim 3, wherein the boundary means determines multiple boundaries based on a plurality of differential expression ratios.

6. The system of claim 5, wherein the filtering means produces data files associated with the plurality of differential ratios.

7. The system of claim 1, wherein the boundary means determines boundaries based on selected magnitudes of the variable expressions.

8. The system of claim 1, wherein the boundary means determines boundaries based on statistics of the data.

9. The system of claim 1, wherein the boundary means determines the boundaries based on selection criteria that provide that a predetermined number of points are located outside the boundaries.

10. The system of claim 9, wherein the boundary means determines a differential expression ratio that produces the boundary lines.

11. The system of claim 1, further including means for processing fluorescence intensity information to produce the points for the scatter plot, with each point representing associated test and control information.

12. The system of claim 1, wherein the means for producing and displaying the scatter plot uses coordinate axis that have selected scales.

13. The system of claimed 12 wherein the axes are logarithmic.

14. A system for analyzing data, the system including:
   A. means for producing and displaying a scatter plot that contains a plotted point for each of the data; and
   B. boundary means for
      i. determining boundaries for segmenting the data based on specified selection criteria and denoting in the scatter plot the points that are located outside of the boundaries,
      ii. determining different boundaries in response to a user interactively specifying corresponding changed selection criteria based on the data points that lie outside of the boundaries previously determined, and for the respective different boundaries denoting in the scatter plot the points that are located outside of the respective different boundaries.

15. The system of claim 14 further including filtering means for collecting the data corresponding to the plotted points that are located outside of the boundaries.

16. The system of claim 15 wherein the filtering means further records the collected data in a computer file.

17. The system of claim 14 wherein the boundary means denotes the points that are located outside of the boundaries by producing the points in a color that differs from color used for the points that are located inside the boundaries.

18. The system of claim 14, wherein the boundary means denotes the points that are located outside of the boundaries by producing the points in an intensity that differs from the intensity used for the points that are located inside the boundaries.

19. The system of claim 14 wherein the boundary means denotes the points that are located outside of the boundaries by using different background color for the areas in which the points are located on the plot.

20. The system of claim 19 wherein the boundary means produces boundary lines that diverge from an x=0, y=0 point and have slopes that are associated with the specified differential expression ratio.

21. The system of claim 19, wherein the boundary means determines boundaries based on a plurality of differential expression ratios.

22. The system of claim 20 further including a filtering means that produces data files associated with the plurality of differential ratios.

23. The system of claim 14, wherein the boundary means determines boundaries based on a specified differential expression ratio of two variable expressions, with one variable expression corresponding to a variable associated with an x-axis and the other variable expression corresponding to a variable associated with a y-axis.

24. The system of claim 14, wherein the boundary means determines boundaries based on selected magnitudes of the variable expressions.

25. The system of claim 14, wherein the boundary means determines boundaries based on statistics of the data.

26. The system of claim 14, wherein the boundary means determines the boundaries based on selection criteria that provide that a predetermined number of points are located outside the boundaries.

27. The system of claim 26, wherein the boundary means determines a differential expression ratio that produces the boundary lines.

28. A system for analyzing data associated with a microarray, the system including:
   A. a fluorescence reader for reading the intensities of microarray dots for both test and control fluorescent wavelengths;
   B. means for producing and displaying a scatter plot that contains a plotted data point for each dot of the microarray, the data points representing test and control fluorescent intensity levels; and
   C. boundary means for
      i. determining boundaries and segmenting the data points based on specified selection criteria that correspond to the particular arrangement of the data points on the scatter plot and denoting in the scatter plot the data points that are located outside of the boundaries,
      ii. receiving changed selection criteria that a user interactively supplies based on both the arrangement of the data points and the segmenting of the data by the boundaries previously determined, and
      iii. determining different boundaries that correspond to the changed selection criteria and denoting in the scatter plot the data points that are located outside the respectiye different boundaries.

29. The system of claim 28 further including filtering means for collecting the data corresponding to the plotted points that are located outside of the boundaries.

30. The system of claim 29 wherein the filtering means further records the collected data in a computer file.

31. The system of claim 28 wherein the boundary means denotes the points that are located outside of the boundaries by producing the points in a color that differs from color used for the points that are located inside the boundaries.

32. The system of claim 28 wherein the boundary means determines boundaries based on a specified differential expression ratio of two variable expressions, with one variable expression corresponding to a variable associated with an x-axis and the other variable expression corresponding to a variable associated with a y-axis.

33. The system of claim 28 wherein the boundary means produces boundary lines that diverge from an x=0, y=0 point and have slopes that are associated with the specified differential expression ratio.

34. The system of claim 32 wherein the boundary means determines boundaries based on a plurality of differential expression ratios.

35. The system of claim 34 further including a filtering means that produces data files associated with the plurality of differential ratios.

36. The system of claim 28 wherein the boundary means determines boundaries based on selected magnitudes of the variable expressions.

37. The system of claim 28 wherein the boundary means determines boundaries based on statistics of the data.

38. The system of claim 28 wherein the boundary means determines the boundaries based on selection criteria that provide that a predetermined number of points are located outside the boundaries.

39. The system of claim 38 wherein the boundary means determines a differential expression ratio that produces the boundary lines.

40. The system of claim 28, wherein the boundary means denotes the points that are located outside of the boundaries by producing the points in an intensity that differs from the intensity used for the points that are located inside the boundaries.

41. The system of claim 28 wherein the boundary means denotes the points that are located outside of the boundaries by using different background color for the areas in which the points are located on the plot.

42. The system of claim 28, wherein the means for producing and displaying the scatter plot uses coordinate axis that have selected scales.

43. The system of claim 42 wherein the axis are logarithmic.

44. A method for producing a scatter plot that defines gene expression data in accordance with user-specified selection criteria, the method including the steps of:
   A. producing and displaying a scatter plot that contains plotted points for the respective gene expression data,
   B. specifying selection criteria that separate the data in the scatter plot into gene expressions of interest and gene expressions not of interest,
   C. determining boundaries that meet the selection criteria specified in step B,
   D. displaying the boundaries of step C in the scatter plot,
   E. interactively specifying a changed set of selection criteria based on the data of interest or the data not of interest as indicated by the boundaries displayed in step D,
   F. determining differentboundaries that meet the changed selection criteria specified in step E,
   G. displaying the boundaries of step F in the scatter plot to indicate corresponding data of interest and data not of interest,
   H. repeating steps E–G for a next set of changed user-specified selection criteria that are based on selecting among the data of interest and the data not of interest that correspond to earlier specified selection criteria.

45. The method of claim 44 further including the step of collecting the data corresponding to the plotted points that are outside of the respective boundaries or inside the respective boundaries.

46. The method of claim 45 wherein the steps of determining the boundaries include determining the boundaries based on respective specified differential expression ratios of two variable expressions, with one variable expression corresponding to a variable associated with an x-axis and the other variable expression corresponding to a variable associated with a y-axis.

47. The method of claim 44, wherein the steps of determining the boundaries include determining the boundaries based on selection criteria that provide that a predetermined number of points are located outside the boundaries.

48. The method of claim 44, wherein the steps of determining the boundaries include determining the boundaries based on statistics of the data.

49. The method of claim 44, wherein the steps of determining the boundaries further include determining a differential expression ratio that produces the boundary lines.

50. The method of claim 44 wherein the steps of determining the boundaries further include using a noise level as a boundary.

* * * * *